United States Patent [19]

Lin et al.

[11] 4,391,690
[45] Jul. 5, 1983

[54] APPARATUS FOR MONITORING $SO_2$ CONCENTRATIONS

[75] Inventors: Ching-Yu Lin, Monroeville; William M. Hickam, Churchill, both of Pa.

[73] Assignee: Westinghouse Electric Corp., Pittsburgh, Pa.

[21] Appl. No.: 181,340

[22] Filed: Aug. 26, 1980

[51] Int. Cl.³ ............................................. G01N 27/58
[52] U.S. Cl. .................................. 204/412; 204/1 T; 204/428
[58] Field of Search ............................. 204/1 F, 195 S

[56] References Cited

U.S. PATENT DOCUMENTS

Re. 28,792  4/1976  Ruka et al. ........................ 204/1 T
3,819,499  6/1974  Johannes et al. ................ 204/195 S

FOREIGN PATENT DOCUMENTS 1002599  12/1976  Canada .
1040264  10/1978  Canada .

OTHER PUBLICATIONS

André M. Chamberland et al., Atmospheric Environment, vol. 11, pp. 257–261, (1977).

Primary Examiner—G. L. Kaplan
Attorney, Agent, or Firm—M. P. Lynch

[57] ABSTRACT

In a solid electrolyte electrochemical cell device for generating an EMF signal based on the Nernst equation which is indicative of the $SO_2$ content of a monitored gas environment, the oxygen content of the reference environment of the cell is adjusted to maintain it equal with the oxygen content of the monitored gas environment to eliminate the effect of oxygen on the EMF signal measurement of $SO_2$.

1 Claim, 3 Drawing Figures

APPARATUS FOR MONITORING SO₂ CONCENTRATIONS

BACKGROUND OF THE INVENTION

The requirements for monitoring and controlling stack gas pollutants have resulted in the development of solid electrolyte gas sensors having compositions uniquely responsive to gaseous pollutants such as $SO_2$. Solid electrolyte sensors for monitoring gases containing anhydrides or related compounds in air or in oxygen bearing gases have been described in detail in Canadian Patents No. 1,002,599 and 1,040,264, both of which have been assigned to the assignee of the present invention and are incorporated herein by reference. The above-referenced sensors are electrochemical cells which generate an EMF signal corresponding to the difference in partial pressure of the monitored gas constituent across the solid electrolyte sensor. Typically, the solid state sensor includes an ion conductive solid electrolyte and electrodes disposed on opposite surfaces thereof. The stack gas, or monitored gas environment, contacts a sensing electrode while the opposite electrode serves as a reference electrode. In order for the EMF signal to be a true indication of the $SO_2$ partial pressure of the monitored gas environment, it is necessary to compensate for, or correct for, variations in the oxygen partial pressure in the monitored gas environment.

Typically, this correction, or compensation, is provided electronically through mathematical manipulation of the EMF output signal of an $SO_2$ measuring solid electrolyte sensor and the EMF output signal of an oxygen measuring solid electrolyte sensor.

SUMMARY OF THE INVENTION

There is disclosed herein with reference to the accompanying drawings several techniques for providing the direct measurement of $SO_2$ concentrations without employing the electronic compensating circuits described above. In the disclosed techniques, the concentration of $O_2$ at the reference electrode of the $SO_2$ solid electrolyte sensor and the $O_2$ concentration at the sensing electrode are kept constant, or equivalent, thus avoiding the requirement for electronically cancelling the effect of varying oxygen concentrations in the monitored gas environment. The desired results are achieved through one of two methods, i.e., mechanical gas mixing, or the electrochemical pumping of oxygen at the reference electrode of the $SO_2$ sensor to maintain a balance between the oxygen concentrations at the sensing and reference electrodes, thereby assuring that the $SO_2$ concentration in the monitored gas environment is directly a function of the EMF output voltage of the $SO_2$ solid electrolyte sensor.

BRIEF DESCRIPTION OF THE DRAWINGS

The invention will become more readily apparent from the following exemplary description in connection with the accompanying drawings.

DESCRIPTION OF THE PREFERRED EMBODIMENT

The high temperature solid electrolyte electrochemical cell disclosed in detail in the above-identified Canadian patents, which are incorporated herein by reference, includes an $SO_2$ sensor which is a solid-sulfate ($K_2SO_4$) galvanic cell of the type:

(reference)          (sensing)

$SO_2$, $O_2$, $Pt/K_2SO_4/Pt$, $O_2$, $SO_2$

The EMF voltage output signal of this solid electrolyte electrochemical cell can be described by the Nernst equation:

$$E_{SO2} = \frac{RT}{2F} \ln (PSO_2)_{total} + \frac{RT}{2F} \ln (PO_2) + C$$

Where $(PO_2)$, and $(PSO_2)_{total} = (PSO_2) + (PSO_3)$ are the partial pressures of sensing gases at the thermodynamic equilibrium. The EMF output voltage, as shown in the above representation of the Nernst equation, is a function of both the $SO_2$ and the $O_2$ partial pressure. In order to monitor the $SO_2$ concentration directly, it is required that the $O_2$ concentration be known or be maintained constant. This can most simply be accomplished by making the reference $O_2$ pressure equivalent to the $O_2$ pressure of the monitored gas environment.

In the above equation, if the oxygen concentration is kept equal at both the reference and sensing electrodes of the $SO_2$ solid electrolyte sensor, the above equation is reduced to:

$$E_{SO2} = \frac{RT}{2F} \ln (PSO_2) + C$$

Thus, the EMF output signal developed by the $SO_2$ solid electrolyte sensor is solely a function of the $SO_2$ concentration of the monitored gas environment contacting the sensing electrode, and the $SO_2$ concentration can be monitored directly from the EMF output signal of the sensor.

Figure 1:
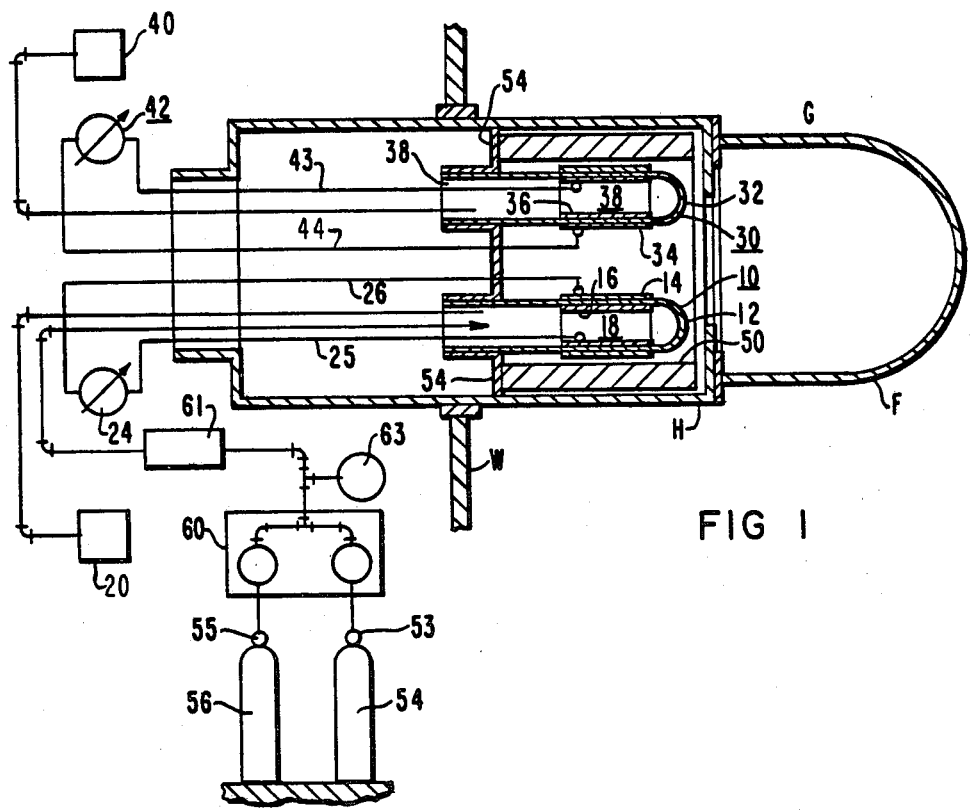
FIG. 1 is a sectioned schematic illustration of an embodiment of the invention based on a mechanical gas mixing technique.
Figure 3:
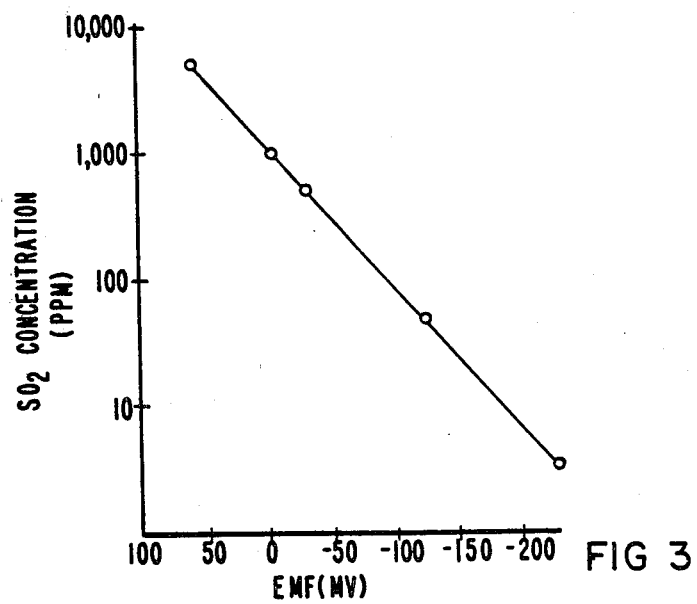
FIG. 3 is a graphical illustration of the operation of the $SO_2$ solid electrolyte sensor employed in the embodiments of FIGS. 1 and 2.

Referring to FIG. 1 there is schematically illustrated a mechanical gas mixing implementation of a technique for compensating for changes in the oxygen concentration of the monitored gas environment G such that the EMF output signal generated by the $SO_2$ solid electrolyte sensor 10 can be monitored directly as an indication of the $SO_2$ concentration of the monitored gas environment G. The embodiment of FIG. 1 includes a tubular housing H having a porous filter member F secured to an open end of the housing H to filter the gas entering the housing H from the monitored gas environment G to prevent potentially damaging particles from contacting the $SO_2$ sensor 10 and the $O_2$ sensor 3. The sensors 10 and 30 are located within a furnace member 50 which maintains the sensors 10 and 30 at a predetermined operating temperature, i.e., between 600° and 1000° C. The steady operating temperature assured by the furnace member 50 eliminates temperature T in the above representation of the Nernst equation from being an unknown variable. The elevated operating temperature is selected to optimize the ionic conductivity of the solid electrolyte members of the sensors 10 and 30. This ionic conductivity is described in detail in the above-referenced Canadian patents for $SO_2$ sensors, and in U.S. Pat. No. Re. 28,792 for oxygen sensors. This U.S. patent is assigned to the assignee of the present invention and is incorporated herein by reference.

The $SO_2$ sensor 10 consists of a solid electrolyte element 12 composed of an alkali metal salt or an alkali-earth metal salt containing oxy-anions of the element forming the anhydride to be detected, namely, $SO_3$. This electrolyte composition and its operation which is typically illustrated in the above cell representation as consisting of $K_2SO_4$ is described in detail in the above-referenced Canadian patents. A sensing electrode 14 is disposed in intimate contact with a surface of the electrolyte 12 which is exposed to the monitored gas environment G passing through the filter F while a reference electrode 16 is disposed in intimate contact with the opposite surface of the electrolyte element 12 and in contact with $SO_2$ reference gas environment. The oxygen sensor 30 consists of an oxygen ion conductive solid electrolyte 32, as described in detail in the above-referenced U.S. patent, having a sensing electrode 34 exposed to the monitored gas environment G entering through filter F and a reference electrode 36 in contact with an oxygen reference environment 38. The sensors 10 and 30 are sealed within the flange member 54 so as to isolate the reference electrodes 16 and 36 from the monitored gas environment G entering through the filter F. The housing H in turn is sealed within the wall structure W of the containment of the monitored gas environment G, which environment may consist of a stack gas environment. The oxygen reference environment may typically be satisfied by supplying air from a suitable source 40 inasmuch as air represents a relatively stable oxygen concentration suitable for serving as an oxygen reference environment for the oxygen sensor 30. A stable $SO_2$ reference 18 is maintained within the sensor 10 in contact with the reference electrode 16 by the reference source 20. The oxygen ion activity of the oxygen sensor 30 is monitored by EMF measuring circuit 42 which is connected to the electrodes 34 and 36 of the sensor 30 by the lead wires 43 and 44. The EMF signal measured by circuit 42 is an indication of the oxygen partial pressure of the gas environment G entering the housing H through the filter F. Similarly, EMF measuring circuit 24, which is connected to the electrodes 14 and 16 of the sensor 10 by lead wires 25 and 26 responds to the ion conductivity of the solid sulfate electrolyte 12 of the sensor 10 by providing an EMF indication of the $SO_2$ concentration of the monitored gas environment G within the housing H.

In the above arrangement, assuming that the oxygen partial pressure at both the sensing electrode 14 and the reference electrode 16 of sensor 10 is equal, the EMF measurement provided by the measuring circuit 24 can be directly interpreted as an indication of the $SO_2$ concentration of the monitored gas environment G entering the housing H through the filter F. However, if the oxygen concentration in the monitored gas environment G varies, as indicated by a change in the EMF measurement of the circuit 42, the oxygen content of the reference gas 18 of the sensor 10 is adjusted to reestablish the balance between the oxygen concentrations at the electrodes 14 and 16. This adjustment of the $O_2$ content of the reference gas 18 is shown in FIG. 1 to be implemented by manually adjusting the control valves 53 and 55 to control the supply of $N_2$ and $O_2$ from the gas sources 54 and 56 respectively to maintain equality between the $O_2$ content of the reference of sensor 10 and the $O_2$ content of the gas environment G. The gas mixer 60 mixes the $N_2$ and $O_2$ and the flow meter 61 measures the flow rate of the reference gas mixture to the sensor 10. The bubbler apparatus 63 exhausts the excess of the reference gas mixture.

Figure 2:
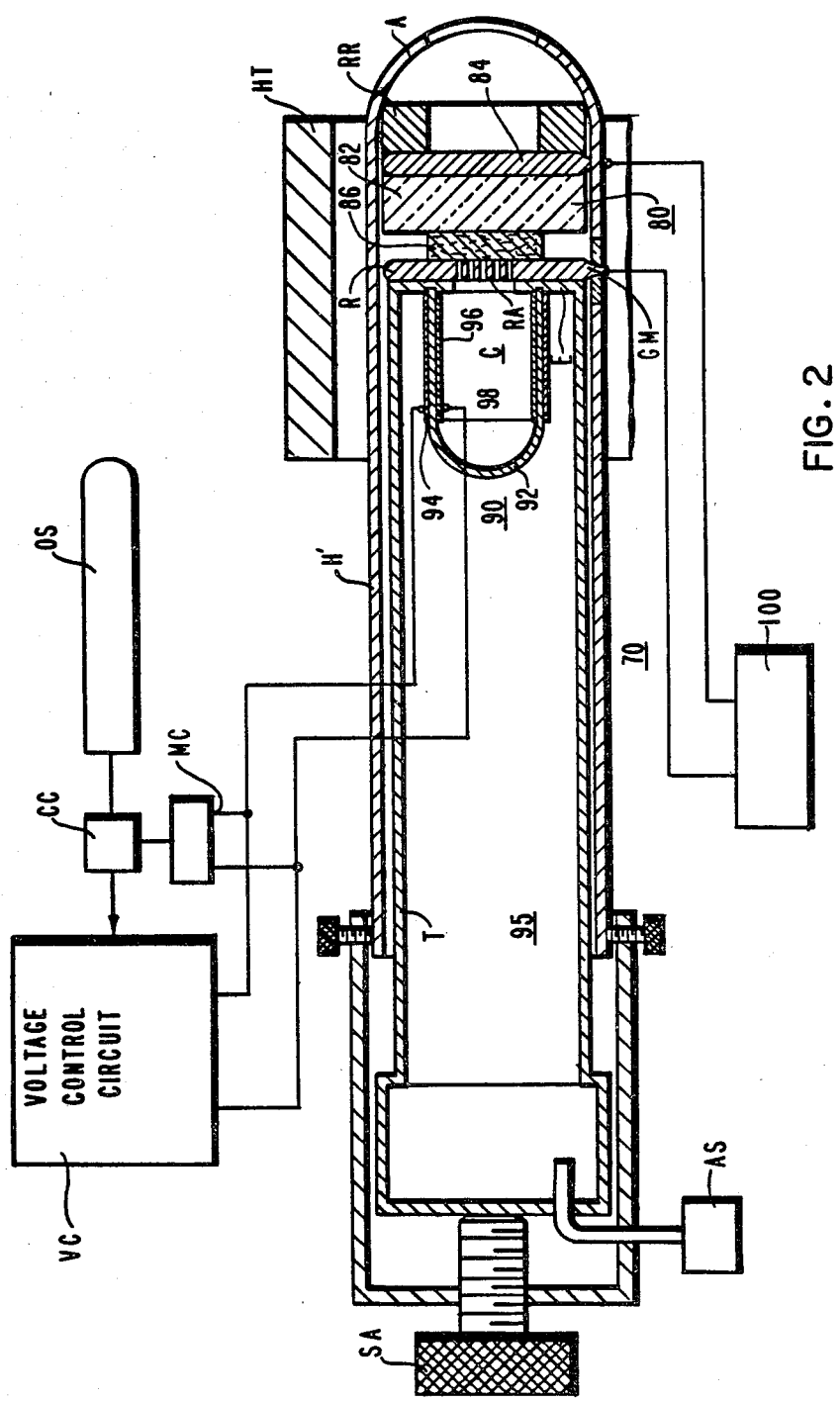
FIG. 2 is a sectioned schematic illustration of an embodiment of the invention based on electrochemical oxygen pumping technique.

A second technique for implementing the oxygen compensation requirements without the gas mixing apparatus of FIG. 1 is schematically illustrated in FIG. 2. An $SO_2$ probe apparatus 70 is illustrated as consisting of the combination of a solid electrolyte $SO_2$ sensor 80 and an oxygen/$SO_2$ reference means consisting of a solid electrolyte oxygen device 90 and an $SO_2$ reference source 98. The $SO_2$ sensor 80 consists of a sodium ion conductive solid electrolyte 82 having a sensing electrode 84 and a reference electrode 86 disposed on opposite surfaces thereof. The composition of the sensor 80 corresponds to that described above with reference to the $SO_2$ sensor 10 of FIG. 1. The solid electrolyte oxygen ion conductive device 90 is configured as consisting of a tubular solid electrolyte member 92 having a closed end and an open end and electrodes 94 and 96 disposed on opposite surfaces thereof. The $SO_2$ sensor 80 and the oxygen ion conductive solid electrolyte cell 90 are mechanically positioned within a metal tubular housing H'. The solid electrolyte oxygen cell 90 extends internally within a movable open ended tubular member T to form a recessed cup-like cavity C within which is positioned an $SO_2$ reference source 98 such as $MgSO_4$. The annular end surface E of the tubular member T to which the oxygen cell 90 compresses a seal ring R having apertures RA therethrough, which may be typically made of gold, into sealing contact with the electrolyte member 82 of the $SO_2$ sensor 80 causing the sensor 80 to be moved into mechanical contact with the retainer ring RR. This sealing motion is in response to the mechanical rotation of the screw adjust mechanism SA which is secured to the opposite end of the tubular member T.

In this configuration, the sensing electrode 84 of the $SO_2$ sensor 80 is exposed to the gas environment G through the aperture A of the housing H' while the reference electrode 86 is isolated from the gas environment G and exposed solely to the reference gas transmitted from the reference gas source 98 through the apertures RA.

The heater apparatus HT establishes the operating temperature of the cells 80 and 90 and heats the reference source 98 ($MgSO_4$) to produce a reference gas composition for the cell 80.

In the disclosed embodiment, the cell 90 functions as an oxygen pump in response to the electrical potential applied to the electrodes 94 and 96 by the voltage control circuit VC. The voltage control circuit VC responds to the EMF output signal of the oxygen sensor OS indicating the oxygen content of the monitored gas environment G by adjusting the polarity of the voltage applied to the electrodes 94 and 96 to assure that the oxygen developed at the reference electrode 86 by the reference source 98 is equal to the oxygen content of the monitored gas environment G. This adjustment eliminates the oxygen factor from the above-described Nernst equation and assures that the EMF signal developed between the electrodes 84 and 86 of the sensor 80, and measured by the EMF measuring circuit 100, is a direct measurement of the $SO_2$ content of the monitored gas environment G.

In the event the oxygen within the cavity C exceeds the oxygen content of the monitored gas environment G as measured by the sensor OS, the polarity of the applied potential from the voltage control circuit VC will be such as to pump, or remove, oxygen from the cavity C through the electrolyte 92 into the internal volume 95 of the tubular member T until the oxygen present at the reference electrode 86 is equal to the oxygen in the monitored gas environment G. A source of oxygen, or air, AS supplies oxygen within the tubular member T to provide a source of oxygen to be pumped into the cavity C in the event the oxygen present at the reference electrode 86 is less than the oxygen present at the sensing electrode 84 of the $SO_2$ sensor 80.

The oxygen supplied within the tubular member T is of a known concentration, i.e., air, and in accordance with the Nernst equation, the EMF measured by the EMF measuring circuit MC is an indication of the oxygen content within the cavity C. This EMF measurement is supplied as an input to a comparator circuit CC with a second input being the EMF output signal from the oxygen sensor OS. The output of the comparator circuit CC indicates whether the oxygen content within the cavity C is greater than, equal to, or less than the oxygen content of the monitored gas environment G. The voltage control circuit VC responds to this output signal by applying a potential across the electrodes 94 and 96 of the oxygen cell 90 to either pump oxygen from the stable oxygen reference environment within the tubular member T or to pump oxygen from the cavity 98 through the electrolyte 92 into the internal volume 95 of the tubular member T until the oxygen within the cavity 98 and contacting the reference electrode 86 is equal to the oxygen content of the monitored gas environment G. Variations in the parts per million oxygen content produced by heating the $MgSO_4$ reference composition are negligible as compared to the significant, i.e., 5-10%, oxygen content of the monitored stack gas environment G.

The metal housing H' serves as an electrical connection for the $SO_2$ measuring circuit to the electrode 84 while an electrical lead passes through a gas to metal seal GM and the housing H' from the gold seal ring R which is in intimate electrical contact with the reference electrode 86.

We claim:
1. Apparatus for measuring the $SO_2$ content of a monitored gas environment, comprising:
   a tubular housing means adapted for positioning within a monitored gas environment having an open end and a means associated with said open end to enable said monitored gas to enter said tubular housing;
   a first solid electrolyte electrochemical cell being positioned within said housing, said first electrochemical cell developing an electrical signal indicative of the combination of the $SO_2$ and the $O_2$ content of said monitored gas environment, said first solid electrolyte electrochemical cell including a sensing electrode exposed to said monitored gas environment and a reference electrode isolated from said monitored gas environment, an $SO_2$ reference environment being maintained in contact with said reference electrode;
   a second solid electrolyte electrochemical cell being positioned within said tubular housing for developing an electrical signal indicative of the oxygen content of the monitored gas environment, said second solid electrolyte electrochemical cell including a sensing electrode exposed to said monitored gas environment and a reference electrode isolated from said monitored gas environment, an oxygen reference environment being maintained in contact with the reference electrode of said second solid electrolyte electrochemical cell;
   monitoring means for measuring electrical signal of said second solid electrolyte electrochemical cell to provide an indication of variations in the oxygen content of said monitored gas environment; and
   a reference gas supply means including a source of oxygen and a source of an inert gas, means for mixing the inert gas and the oxygen gas and means for adjustably supplying said gas mixture to the reference electrode of said first solid electrolyte electrochemical cell to compensate for changes in the oxygen content of the monitored gas environment such that the electrical signal developed by said first solid electrolyte electrochemical cell is a measurement of the $SO_2$ content of the monitored gas environment.

* * * * *